United States Patent
Hidaka et al.

[11] Patent Number: 6,153,798
[45] Date of Patent: Nov. 28, 2000

[54] CATALYSTS FOR METHANOL CONVERSION REACTIONS

[75] Inventors: Toshio Hidaka; Emiko Yokose, both of Tsukuba, Japan

[73] Assignee: Mitsubishi Gas Chemical Co., Ltd., Tokyo, Japan

[21] Appl. No.: 09/121,307

[22] Filed: Jul. 23, 1998

[30] Foreign Application Priority Data

| Jul. 23, 1997 | [JP] | Japan | 9-197232 |
| Dec. 26, 1997 | [JP] | Japan | 9-360124 |
| Feb. 6, 1998 | [JP] | Japan | 10-025832 |

[51] Int. Cl.⁷ .................................................. C07C 209/16
[52] U.S. Cl. .......................... 564/479; 502/208; 502/214
[58] Field of Search .............................................. 564/479

[56] References Cited

U.S. PATENT DOCUMENTS

| 4,205,012 | 5/1980 | Parker . |
| 4,313,003 | 1/1982 | Weigert . |
| 4,436,938 | 3/1984 | Tompsett . |
| 5,126,308 | 6/1992 | Barger . |
| 5,248,647 | 9/1993 | Barger . |
| 6,069,280 | 5/2000 | Van Gysel et al. ............... 564/479 |

FOREIGN PATENT DOCUMENTS

| 0 025 693 | 9/1980 | European Pat. Off. . |
| 0 103 117 | 7/1983 | European Pat. Off. . |
| 0 105 512 | 10/1983 | European Pat. Off. . |
| 0 159 624 | 4/1985 | European Pat. Off. . |
| 0 161 488 | 4/1985 | European Pat. Off. . |
| 0 161818 A2 | 11/1985 | European Pat. Off. . |
| 0 210 718 | 4/1986 | European Pat. Off. . |
| 0 324 267 | 12/1988 | European Pat. Off. . |
| 0 600483 A1 | 6/1994 | European Pat. Off. . |
| 58-49340 | 3/1983 | Japan . |
| 59-210050 | 11/1984 | Japan . |
| 59-227841 | 12/1984 | Japan . |

*Primary Examiner*—Johann Richter
*Assistant Examiner*—Brian J. Davis
*Attorney, Agent, or Firm*—Pillsbury Madison & Sutro LLP

[57] ABSTRACT

Dimethylamine is prepared from a reaction of methanol with ammonia or monomethylamine or a disproportionation reaction of monomethylamine, in the presence of a catalyst of silica-modified crystalline silicoaluminophosphate molecular sieve or silica-modified SAPO.

6 Claims, 1 Drawing Sheet

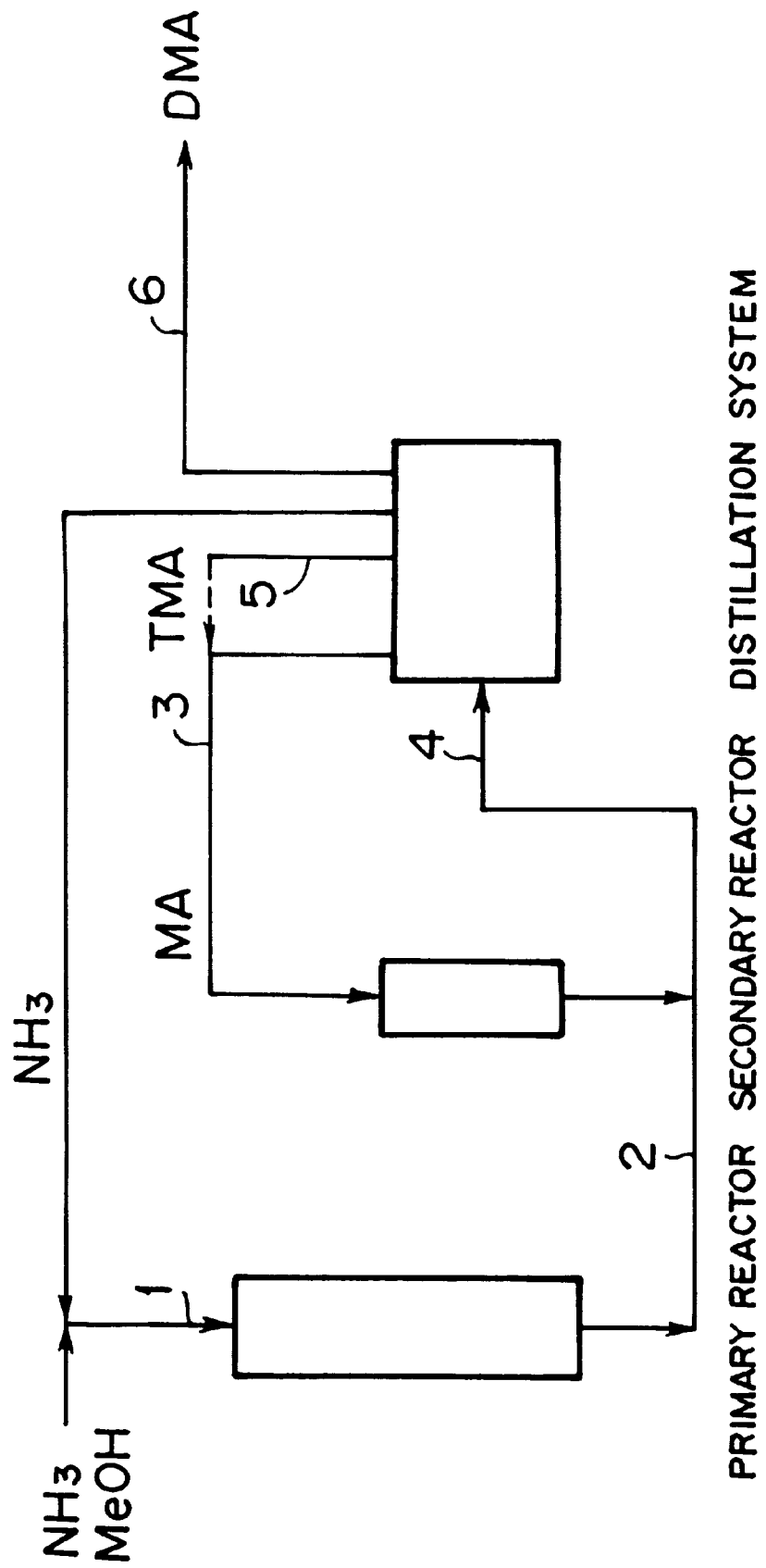

CATALYSTS FOR METHANOL CONVERSION REACTIONS

BACKGROUND OF THE INVENTION

1. Field of the Invention

This invention relates to a silica-modified silicoaluminophosphate catalyst, a method for preparing the same, and a process for producing methylamines or lower olefins through a methanol conversion reaction using the same. More particularly, the invention relates to a silica-modified silicoaluminophosphate catalyst which is useful for various catalytic reactions, including production of methylamines through a reaction of methanol with ammonia or monomethylamine, production of dimethylamine through a disproportionation reaction of monomethylamine, and production of lower olefins from methanol, and a method for preparing such catalysts, as well as a process for producing methylamines or lower olefins using such catalysts.

Methylamines, specifically dimethylamine, are important materials for production of solvents, typically dimethylformamide, rubber products, pharmaceuticals, surfactants and others. Lower olefins are key materials in the chemical industry.

2. Description of the Related Art

Using methanol which is obtained from natural gas on a large scale at a moderate cost, many efforts have so far been made to convert it to useful chemicals, for example, olefins, ethylene glycol, ethanol, etc. However, these have not yet been successfully conducted on a commercial scale. Important, commercially available methanol derivatives involve formaldehyde and methylamines. It has already been known that methylamines and olefins are produced from methanol by using silicoaluminophosphate molecular sieves as a catalyst. Methylamines have generally been produced from methanol and ammonia at a temperature around 400° C. using a solid catalyst such as silica-alumina. It has also been known that methylamines can be produced from methanol and other methylamines, or through disproportionation of monomethylamine. In these processes for producing methylamines, however, the main product is trimethylamine for which there is little demand in the marketplace. Thus, a process for producing dimethylamine in a higher selectivity has been desired, because of its biased demand among three methylamines.

In recent years, a number of methods for producing methylamines using zeolite catalysts have been proposed, which are more advantageous as compared with the silica-alumina catalysts used so far. For example, there are methods using zeolites, such as zeolite A (JP 56-69846A); FU-1 (JP 54-148708A); ZSM-5 (U.S. Pat. No. 4,082,805); ferrierite and erionite (JP 59-113747A); ZK-5, RHO, chabazite and erionite (JP 61-254256A); and mordenite (JP 56-46846A, JP 58-49340A, JP 59-210050A and JP 59-227841A). Also, a method for producing monomethylamine and the like in an amount exceeding the thermodynamic equilibrium proportion by using a silicoaluminophosphate has been proposed (JP 2-734A).

Meanwhile, ethylene, propylene and other important olefins can be derived from methanol by using zeolites and silicoalumino-phosphates as a catalyst, and a number of methods have been proposed after active studies. Among them, a silicoaluminophosphate catalyst, for example, SAPO-34 catalyst developed by UOP (JP 59-84829A), has been well known from its excellent performances. However, SAPO-34 has small pore diameters of approximately 0.4 nm, and necessitates a high reaction temperature of 400 to 450° C., thereby being suffered from coking, with a short catalyst life of several hours. When the silicoaluminophosphates are prepared according to the conventional methods disclosed in literatures, for example, JP 59-35018A, JP 60-251122A and JP 60-260420A, the products are not free from some disadvantages, such as the long crystallizing period of time, a large amount of impurities, and a low degree of crystallization due to the remaining amorphous components. Furthermore, the silicoaluminophosphates thus prepared have insufficient performances as a methylamine catalyst, in respect to methanol conversion ratio and dimethylamine selectivity, and also as a lower olefin catalyst, in respect to activity, selectivity and catalyst life.

SUMMARY OF THE INVENTION

An object of the invention is to provide for a catalyst for producing methylamines which is free from the disadvantages as seen in the conventional catalysts, a method for preparing said catalyst, and a process for producing methylamines or lower olefins through a methanol conversion reaction by using said catalyst.

After having made extensive studies on the more economical processes for producing chemicals derived from methanol, for example, dimethylamine and lower olefins, as well as the catalysts commercially usable for that purposes, the present inventors have finally accomplished the present invention. They find that a crystalline silicoaluminophosphate catalyst prepared according to definite steps and then modified with silica as mentioned below surprisingly exhibits a high methanol conversion ratio and an excellent dimethylamine selectivity in the production of methylamines, particularly dimethylamine, from methanol and ammonia or monomethylamine. Furthermore, said catalyst also exhibits an excellent selectivity in the conversion of methanol to lower olefins, along with the other unexpected results, such as longer catalyst life than in conventional ones.

Accordingly, the invention provides a silica-modified crystalline silicoaluminophosphate catalyst which is applicable to various catalytic reactions, including production of methylamines, mainly dimethylamine, through a reaction of methanol with ammonia or monomethylamine, or through a disproportionation reaction of methylamines, and production of lower olefins such as ethylene and propylene from methanol. The present invention further provides a method for preparing such catalysts. The present invention further provides a process for producing methylamines or lower olefins through a methanol conversion reaction using such catalysts.

More particularly, the catalysts according to the invention are crystalline silicoaluminophosphate molecular sieves modified with silica. The crystalline silicoaluminophosphate molecular sieves contain as the main constituent at least one member selected from the group consisting of SAPO-5, 11, 17, 18, 26, 31, 33, 34, 35, 42, 43, 44, 47 and 56. The relationship between the number of a SAPO and the structure of the SAPO is described in Encyclopedia of Inorganic Chemistry, Vol. 8, 4369 (1994). The crystalline silicoaluminophosphate molecular sieves are of H-type, or that partially replaced by atoms selected from the group consisting of Li, Ti, Zr, V, Cr, Mn, Fe, Co, Zn, Be, Mg, Ca, B, Ga and Ge. Mole ratio of the silica constituent in the crystalline silicoaluminophosphate is in the range of from 0.02 to 0.5, based on mole of the alumina.

The catalysts of the present invention are prepared by modifying the crystalline silicoaluminophosphate molecular sieves with silica. The silica-modification is effected, for example, by treating the catalyst with a Si-source compound, thereby silicon atoms being accumulated, precipitated or coated on the surface, by vapor phase silane treatment through chemical vapor deposition (CVD) using silicon tetrachloride, or by silane treatment with an organic silicon compound.

Further, the crystalline silicoaluminophosphates may be prepared by addition of an aluminum alkoxide to an aqueous amine or organic ammonium salt solution cooled to a temperature of not higher than 20° C., followed by hydrolysis, until a uniform aqueous aluminum hydroxide colloid or solution is produced; addition, to the colloid or solution, of silica or other Si-source compound, and phosphoric acid or other P-source compound, if desired, along with a metal source selected from the group of Li, Ti, Zr, V, Cr, Mn, Fe, Co, Zn, Be, Mg, Ca, B, Ga and Ge, and then hydrothermal treatment of the resulting mixture. In other words, the crystalline silicoaluminophosphates are those prepared by hydrothermally treating a material mixture consisting of oxides, an amine and water as shown in the formula (1):

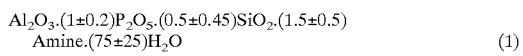

$$Al_2O_3 \cdot (1 \pm 0.2)P_2O_5 \cdot (0.5 \pm 0.45)SiO_2 \cdot (1.5 \pm 0.5) \\ Amine \cdot (75 \pm 25)H_2O \qquad (1)$$

wherein "Amine" means an amine or organic ammonium salt having 1 to 16 carbon atoms.

BRIEF DESCRIPTION OF THE DRAWING

The accompanying drawing shows a reaction process used in Example 14 and Comparative Example 10. In the FIGURE, a mark 1 is a flowing passage for feeding materials to the primary reactor; 2, a flowing passage; 3, a flowing passage for feeding materials to the secondary reactor; 4, a flowing passage; 5, a flowing passage for trimethylamine; and 6, a flowing passage for dimethylamine. MeOH, MA, DMA and TMA means methanol, monomethylamine, dimethylamine and trimethylamine, respectively.

DESCRIPTION OF THE PREFERRED EMBODIMENTS

The material crystalline silicoaluminophosphate molecular sieves which are to be silica-modified according to the invention are, as disclosed in, for example, JP 57-77015A, those in which a crystalline aluminum phosphate compound (ALPO) having a chemical composition of the formula (2) when represented by mole ratio of oxides excepting the crystal water and an organic base as templating agent, is isomorphically replaced at a part of P or Al—P linkage with Si, and typically referred to as SAPOs.

$$Al_2O_3 \cdot (1.0 \pm 0.2)P_2O_5 \qquad (2)$$

As such crystalline silicoaluminophosphates, there are mentioned, for example, SAPO-5, 11, 17, 18, 26, 31, 33, 34, 35, 37, 40, 41, 42, 43, 44, 47 and 56, as well as those isomorphically replaced by Li, Ti, Zr, V, Cr, Mn, Fe, Co, Zn, Be, Mg, Ca, B, Ga or Ge.

In order to obtain dimethylamine selectively, the minimum effective micropore diameter of the molecular sieves is preferably within the range of 0.3 to 0.6 nm. According to the IUPAC structural code of zeolitic compounds, ABW, AEI, AFX, APC, ATN, ATT, ATV, AWW, CHA, DDR, EAB, ERI, GIS, JBW, KFI, LEV, LTA, MER, MON, PAU, PHI, RHO, RTE, RTH, and VNI of 8-membered ring structure; CHI, LOV, RSN, and VSV of 9-membered ring structure; DAC, EPI, FER, LAU, MEL, MFI, MFS, MTT, NES, TON, and WEI of 10-membered ring structure; and AFS, AFY, ATO, CAN, GME, MAZ, MEI, MTW, OFF, RON, and VET of 12-membered ring structure can be mentioned, and SAPOs corresponding to these structures are particularly preferred. Specifically, SAPO-5, 11, 17, 18, 26, 31, 33, 34, 35, 37, 40, 41, 42, 43, 44, 47 and 56 are mentioned, among which particularly preferable are SAPO-5, 11, 17, 18, 26, 31, 33, 34, 35, 42, 43, 44, 47 and 56. The crystalline silicoaluminophosphate molecular sieves may be of H-type, or that partially replaced by atoms selected from the group of Li, Ti, Zr, V, Cr, Mn, Fe, Co, Zn, Be, Mg, Ca, B, Ga and Ge. Such crystalline SAPOs can readily be prepared from an aluminum compound, an aqueous phosphate solution with an Si-source compound, and an amine or quaternary ammonium compound as templating agent.

Methods for preparing crystalline silicoaluminophosphate molecular sieves, which are the materials for preparing the silica-modified crystalline silicoaluminophosphate molecular sieves of the present invention, are generally known in the art, for example, as disclosed in JP 59-35018A. In order to secure the molecular sieve catalysts having excellent characteristics for producing methylamines or lower olefins according to the invention, however, it is necessary to control the sequence of addition of materials and the temperature range. If the temperature is higher than 20° C., crystalline aluminum hydroxide tends to form and may remain as impurity. Accordingly, preferable temperatures are not higher than 20° C. Thus, it is desirable to prepare the catalyst by making a uniform aqueous aluminum hydroxide colloid or solution through addition of an aluminum alkoxide to an aqueous amine or organic ammonium salt solution at a temperature of 0 to 10° C., followed by hydrolysis, then adding, to the colloid or solution, silica or other Si-source compounds, and phosphoric acid or other P-source compounds, if desired, along with a metal source selected from the group of Li, Ti, Zr, V, Cr, Mn, Fe, Co, Zn, Be, Mg, Ca, B, Ga and Ge, and hydrothermally treating the resulting mixture.

The preferable aluminum sources used for the material include pseudoboehmite and aluminum alkoxide having 3 to 24 carbon atoms, among which aluminum isopropoxide is the most preferable. The preferable Si-sources include silica, silica sol and ortho-silicic acid. The particularly, though not exclusively, preferable P-source includes ortho-phosphoric acid. The preferable templating agents include amines and organic ammonium salts having 3 to 24 carbon atoms. For example, there are mentioned trimethylamine, triethylamine, triethanolamine, isopropylamine, dibutylamine, dipentylamine, dihexylamine, piperidine, choline, morpholine, cyclohexylamine, 2-methylpyridine, 4-methylpyridine, tripropylamine, quinuclidine, N-methylcyclohexylamine, N,N-dimethylbenzylamine, N,N-dimethylethanolamine, N,N-diethyl-ethanolamine, N,N-dimethylpiperazine, tetraethylammonium hydroxide, tetrapropylammonium hydroxide, tetrabutylammonium hydroxide and the like.

The metal sources, which may be added if desired, are preferably water-soluble salts, such as nitrate, sulfate and chloride, of the desired metals.

Particularly preferable composition of the material mixture for preparing the crystalline silicoalumino-phosphates ranges 0.8 to 1 mole of $P_2O_5$, 0.05 to 0.95 mole of silica, 0.5 to 2 moles of amine templating agent and 50 to 100 moles of water, based upon one mole of alumina. The composition of the material mixture is preferably so adjusted that the mole ratio of silica to alumina in the resulting crystalline silicoalumino-phosphate molecular sieve is within the range of 0.02 to 0.5.

For the hydrothermal treatment of the material mixture, the reaction is effected preferably in a Teflon-lined pressure vessel at a temperature of 100 to 250° C. under autogenous pressure usually for 1 to 200 hours to obtain crystalline silicoaluminophosphate. Then, formed crystals are separated by filtration, decantation or centrifugation. Then, they are desirably washed well with water until the washings become neutral The crystals are dried generally at a temperature of 80 to 150° C., and then calcinated at a temperature of 350 to 700° C., preferably 500 to 600° C., in a stream of the air or other oxidizing atmosphere.

The crystalline silicoaluminophosphate molecular sieves thus prepared are particularly, though not exclusively, useful as catalyst for the reaction of methanol with ammonia or monomethylamine. The crystalline molecular sieves above are also useful for the conversion of methylamines such as monomethylamine to dimethylamine through a disproportionation reaction. Furthermore, the crystalline molecular sieves above are useful as a catalyst for the production of lower olefins from methanol. However, in order to attain an improved selectivity and life as catalyst, the crystalline silicoaluminophosphate molecular sieves are better subjected further to an immersion treatment using, for example, mineral acids or chelating agents, a steam heating treatment, or a silica-modification, among which the silica-modification is the most effective.

The silica-modification is effected, for example, by treating the catalyst with an Si-source compound, thereby Si atoms being accumulated, precipitated or coated at the surface, by vapor phase silane treatment through CVD using silicon tetrachloride, or by a silane treatment with an organic silicon compound. Among them, the silane treatment with an organic silicon compound is preferable, and a simple liquid phase silane treatment is particularly preferable.

Organic silicon compounds used for the silane treatment include alkyl- or arylsilanes such as triethylsilane, methylphenylsilane, phenylsilane, diphenylsilane and triethylsilane; chlorosilanes such as methyldichlorosilane, ethylmethylchlorosilane, dimethyldichlorosilane and phenylmethylchlorosilane; alkoxysilanes such as trimethoxysilane, tetramethoxysilane, triethoxysilane, tetraethoxysilane, diethoxymethylsilane and allyloxytrimethylsilane; silylamines such as N,N-dimethylaminotrimethylsilane, N,N-dimethylaminodimethylsilane and tris(N,N-dimethylamino) methylsilane; and silylamides such as N,O-bis (trimethylsilyl)acetamide, N-trimethylsilylacetamide and bistrimethylsilylurea. Among them, cholorosilanes and alkoxysilanes are preferable, because of their economical costs, particularly alkoxysilanes being most preferred. In the silica-modification through the silane treatment, it is more effective that the crystalline molecular sieves are adequately subjected to a treatment in advance, such as a treatment by steam heating at a temperature of 250 to 750° C., a treatment by immersion using an acid, amine or chelating agent, and a suitable moisture-controlling treatment.

It is not so easy to sweepingly define the conditions for the silane treatment, but the treatment may be effected, for example, at a temperature from ambient to 700° C., for not longer than 96 hours of immersion period of time, under a pressure of not higher than 0.1 or not higher than 30 MPa in a gaseous or liquid phase or under supercritical state. In order to secure the efficient silane treatment, an immersion treatment, shaking under heating, supersonic dispersion, etc. in a suitable solvent, such as alcohols, esters and hydrocarbons, may suitably be conducted. There is no limitation in the concentration of the silane treating agent, but, usually a concentration ranging 1 to 30% by weight suffices.

After the silane treatment, the catalyst is separated by filtration, washed, dried and then calcined at a temperature of 400 to 750° C. for 2 to 24 hours, preferably in an oxidative atmosphere, to improve the catalytic activity and selectivity.

The silica-modified catalysts thus prepared may be used as they are. Alternatively, they may be in combination with other aluminosilicate molecular sieves, which have been silica-modified in a similar way, such as chabazite, mordenite, erionite, ferrierite, epistilbite, clinoptilolite, paulingite, phillipsite, levynite, zeolite-A, RHO, ZK-5, FU-1 and ZSM-5. These catalysts may be shaped as they are. Alternatively, shaping may be made with a suitable binder clay mineral, such as kaolinite, halloysite, nacrite, montmorillonite, illite, etc. The shaped products are used for various reactions, for example, for production of methylamines and lower olefins.

The silica-modified silicoaluminophosphate molecular sieves are used as a catalyst for the production of methylamines through a reaction of methanol with ammonia or monomethylamine, or through a disproportionation reaction of monomethylamine, or for production of lower olefins from methanol. These reactions are preferably conducted on a gas phase fixed bed, or by passing through a fluidizing bed, but the present invention is not limited to such ways of reactions.

In the production of methylamines through a reaction of methanol with ammonia or monomethylamine, or through disproportionation of monomethylamine, a reaction temperature within the range of 200 to 400° C. is preferable, particularly, 250 to 350° C. being more preferable. There is no limitation in the reaction pressure. Thus, it may be from reduced to superatmospheric pressure. Preferably, the reaction is conducted within the pressure range of 0.1 to 10 MPa.

For the production of dimethylamines, which is the most important among methylamines, from methanol and ammonia, the following process is preferable. Thus, the process comprises two steps, i.e., a Step 1 in which a material mainly composed of methanol and ammonia is subjected to a reaction over a catalyst to form methylamines containing monomethylamine and dimethylamine, and a Step 2 in which the monomethylamine obtained in the Step 1 is subjected to a disproportionation reaction over a catalyst to convert it to dimethylamine. A silica-modified crystalline silicoaluminophosphate molecular sieve is used as a catalyst in at least one of the Steps 1 and 2.

The process is conducted in a primary reactor for Step 1 and in a secondary reactor for Step 2. In Step 1, a material mainly composed of methanol and ammonia is subjected to a reaction over a catalyst to form methylamines containing monomethylamine and dimethylamine. After the reaction is over, recovery of ammonia containing monomethylamine, recovery of trimethylamine, dehydration, and then recovery of monomethylamine and dimethylamine, are conducted. These recoveries are effected generally through distillation. The recovered ammonia and trimethylamine are recycled to the primary reactor in Step 1. The recovered monomethylamine is fed to the secondary reactor in Step 2 for conversion to dimethylamine through a disproportionation reaction. Though it is possible to recycle the recovered monomethylamine into the primary reactor for the disproportionation, preference is that the secondary reactor for the disproportionation is provided for efficient conversion of the recovered monomethylamine to dimethylamine. Thus, objective dimethylamine formed in Steps 1 and in 2 is recovered. The reactions in Steps 1 and in 2 are preferably conducted on a gas phase fixed bed, or by passing through a fluidizing bed, but the invention is not limited to such ways of reactions. The primary reactor and the secondary reactor may be installed each in single or plural.

The materials in Step 1 are methanol and ammonia, which may contain dimethyl ether or methylamines. The material in Step 2 is monomethylamine, which may contain methanol and dimethyl ether along with other methylamines. In each of Steps 1 and 2, the reaction is preferably effected at a temperature of 200 to 400° C. A temperature of 250 to 350° C. is particularly preferable from the viewpoints of dimethylamine selectivity and catalyst activity. The catalysts filled in the primary reactor and in the secondary reactor may be the same or different from each other. The catalyst is preferably filled as a single layer or in a number of layers. Particularly preferable is that in which a number of layers filled with a catalyst are provided and the material is separately supplied to each of the plural catalyst layers, from the viewpoints of removal of reaction heat, prevention of side reactions due to temperature elevation in the catalyst layer, and avoidance of catalyst life deterioration.

Reaction pressures in Step 1 and in Step 2 are preferably within the range of 0.1 to 10 MPa, more preferably 0.5 to 2 MPa. As for material feeding rates (GHSV 1/h) in Step 1 and in Step 2, a higher rate is preferred from the viewpoint of productivity, but too high rate causes decrease in the material conversion ratio. In this invention, a GHSV of 100 to 10,000 per hour is generally preferable. Under the reaction conditions as above, a methylamine mixture is obtained at an outlet of the primary reactor, said mixture having a composition usually containing 20 to 40% by weight of monomethylamine and 60 to 80% by weight of dimethylamine based on a total amount of methylamines. There is few amount of trimethylamine in the methylamine mixture. Accordingly, the yield of dimethylamine is further improved by providing the Step 2 in which monomethylamine is effectively converted to dimethylamine.

For the production of lower olefins having 2 to 4 carbon atoms from methanol, the feeding material is methanol, dimethyl ether, or a mixture thereof. Water, nitrogen or other inert gas may be accompanied in order to accelerate the reaction or to prevent the retention. A reaction temperature within the range of 250 to 500° C., particularly, 350 to 450° C., is preferable. There is no limitation for the reaction pressure, and the reaction can be conducted under a reduced to superatmospheric pressure. Normally, a pressure ranging from 0.01 to 10 MPa is preferable.

EXAMPLES

The invention will more fully be described with respect to the following Examples, Reference Example and Comparative Examples. In these Examples and Comparative Examples, the reaction is allowed to proceed in a flowing reaction apparatus provided with a material tank, a material-feeding pump, an inert gas introducing device, reactors (made of SUS 316L, 13 φ inner diameter and 300 mm length), a sampling tank, back pressure valves, etc. Two to four hours after the reaction reaches the stationary conditions, samples are taken during about 1 hour, which were analyzed by gas chromatography to estimate the composition distribution of the products.

Catalyst Preparation 1
  Silica-modified SAPO-34:
  To a mixture of 151.47 g of an aqueous 35% tetraethylammonium hydroxide solution and 84.2 g of pure water, cooled to 0° C., was added 81.7 g of aluminum isopropoxide portionwise over 3 minutes, and the mass was subjected to high speed stirring for 15 minutes. Then, 12 g of silica sol was added thereto, and the mass was subjected to a high speed stirring for 5 minutes to form a uniform reaction mass, to which 46.1 g of 85% phosphoric acid was added. After 5 minutes stirring as above, the mass was subjected to a trituration treatment for 1 hour. The resulting mixture was heated in an autoclave at 200° C. for 4 hours, and the solid product was separated by centrifugation, washed with water 4 times, dried overnight at 110° C., and then calcined in the air at 600° C. for 4 hours, to give 40 g of colorless crystalline powder. An XRD analysis of the powder exhibited a diffraction pattern of SAPO-34. The product had a high crystallinity with uniform and even particle size according to scanning electron microscope (SEM) observation. The water content of the crystalline product was adjusted to 10% by weight, and the product was immersed in a dry toluene solution containing 13% of tetraethoxysilane (TEOS) for 16 hours. Then, the crystals were separated by filtration, dried in vacuo at 120° C. for 4 hours, and then calcined at 600° C. for 3 hours in the air to give 37.9 g of the entitled silica-modified SAPO-34 (Catalyst 1).

Catalyst Preparation 2
  Silica-modified SAPO-17:
  The procedure was repeated in similar way as in Catalyst Preparation 1, except that the tetraethylammonium hydroxide as templating agent was replaced by cyclohexylamine. After hydrothermal treatment at 200° C. for 24 hours, 35 g of crystalline powder was obtained. A sharp pattern of XRD diffraction exhibited that the highly crystalline product was SAPO-17, which was then subjected to a silane treatment in similar way as in Catalyst Preparation 1 to give the entitled silica-modified SAPO-17 (Catalyst 2).

Catalyst Preparation 3
  Silica-modified SAPO-18:
  To a mixture of 49.0 g of an aqueous 40% tetraethylammonium hydroxide solution and 36 g of pure water, cooled to 0° C., was added 27.2 g of aluminum isopropoxide portionwise over 3 minutes, and the mass was subjected to high speed stirring for 15 minutes. Then, 0.2 g of 37% hydrogen chloride was dropped, 12 g of a silica sol was added thereto, and the mass was subjected to high speed stirring for 5 minutes to form a uniform reaction mass, to which 15.1 g of 85% phosphoric acid was added. After 5 minutes stirring as above, the mass was subjected to a trituration treatment for 1 hour. The resulting mixture was heated in an autoclave at 200° C. for 120 hours, and the solid product was separated by centrifugation, washed with water 4 times, dried overnight at 110° C., and then calcined in the air at 600° C. for 4 hours, to give 40 g of colorless crystalline powder. An XRD analysis of the powder exhibited a diffraction pattern of SAPO-18. A silane treatment in similar way as in Catalyst Preparation 1 gave the entitled silica-modified product (Catalyst 3).

Catalyst Preparation 4
  Silica-modified CoSAPO-34:
  The procedure was repeated as in Catalyst Preparation 1, except that 2.5 g of cobalt acetate was added as a metal source, to give cobalt-containing SAPO-34, which was silane-treated as in above, to give the entitled silica-modified CoSAPO-34 (Catalyst 4).

Catalyst Preparation 5
  Silica-modified TiSAPO-34:
  The procedure was repeated as in Catalyst Preparation 4, except that titanium isopropoxide as a Ti-source was used in place of the cobalt acetate, to give TiSAPO-34, which was then silane-treated to give the entitled silica-modified product (Catalyst 5).

Catalyst Preparation 6
  To a mixture of 151.47 g of an aqueous 35% tetraethylammonium hydroxide solution and 84.2 g of pure water, kept at 30° C., was added 81.7 g of aluminum isopropoxide portionwise over 3 minutes, and the mass was subjected to high speed stirring for 15 minutes. Then, 12 g of a silica sol was added thereto, and the mass was subjected to high speed stirring for 5 minutes to form a uniform reaction mass, to which 46.1 g of 85% phosphoric acid was added. After 5 minutes stirring as above, the mass was subjected to a trituration treatment for 1 hour. The resulting mixture was heated in an autoclave at 200° C. for 4 hours, and the solid product was separated by centrifugation, washed with water 4 times, dried overnight at 110° C., and then calcined in the air at 600° C. for 4 hours, to give 40 g of colorless crystalline powder. An XRD analysis of the powder exhibited a diffraction pattern of SAPO-34, but the pattern is not so sharp, which exhibits a low crystallinity. According to SEM observation, the particle size is uneven and the presence of impurities was recognized. The crystals were silane-treated in similar way as in Catalyst Preparation 1, to give silica-modified SAPO-34 (Catalyst 6).

Catalyst Preparation 7

According to the prior art disclosed in JP 59-35018A, a catalyst was prepared as follows: To a mixture of 51.3 g of 85% phosphoric acid and 160 g of water was added 90.7 g of aluminum isopropoxide under stirring. Furthermore, 12 g of a 30% by weight silica sol was added thereto, and the mixture was stirred to form a uniform mass, to which 27.2 g of an aqueous 40% tetraethylammonium hydroxide solution was added. After mixing under stirring, the resulting mixture was heated in an autoclave at 200° C. for 40 hours. The solid product was separated by centrifugation, washed 4 times with water, dried overnight at 110° C., and calcined at 600° C. in the air for 4 hours, to give 40 g of colorless crystalline powder. An XRD analysis of the powder exhibited a diffraction pattern of SAPO-34, but the pattern is not so sharp when compared with that in Catalyst 1, and the degree of crystallinity is small. SEM observation exhibited that crystalline particles are uneven. The crystals were adjusted to 10% by weight moisture content, and immersed in a dry toluene solution containing 13% of tetraethoxysilane (TEOS) for 16 hours. Thereafter, the crystals were separated by filtration, dried at 120° C. in vacuo for 4 hours, and then calcined in the air at 600° C. for 3 hours, to give silica-modified SAPO-34 (Catalyst 7).

Comparative Catalyst Preparation 1

Mordenite (SiO2/Al$_2$O$_3$=16) was used as the molecular sieve, which was silane-treated in similar way as above, to give silica-modified mordenite (to be used in Comparative Example 9).

(Production of Methylamines)

Example 1

Into a reactor filled with 4.5 g (10 ml volume) of Catalyst 1 was fed a material mixture (methanol:ammonia=1:1) at a rate of 15 g per hour with a space velocity (GHSV:1/h) of 1,500, and the reaction was allowed to proceed at a temperature of 320° C. under a pressure of 2 MPa. Methanol conversion ratio was 99.4%, and the selective ratios of mono-, di- and trimethylamine were 35%, 63% and 2% by weight, respectively.

Example 2

Procedure in Example 1 was repeated, except that the space velocity was 3,500, instead of 1,500. Methanol conversion ratio was 93.1%, and the selective ratios of mono-, di- and trimethylamine were 38%, 61% and 1% by weight, respectively.

Example 3

Procedure in Example 1 was repeated, except that the space velocity was 5,000, instead of 1,500. Methanol conversion ratio was 90.4%, and the selective ratios of mono-, di- and trimethylamine were 43%, 57% and 0% by weight, respectively.

Reference Example 1

Results from a methylamine conversion reaction shown in Example 3 described in JP 59-227841A, which is one of prior arts using a steam-treated Na-mordenite catalyst, are reproduced herein.

| Reaction temperature: | 320° C. | |
|---|---|---|
| Pressure: | 1.8 MPa | |
| Material composition: | a same amount mixture of methanol and ammonia | |
| Space velocity (1/h): | 1420 | 4280 |
| Methanol conversion (%): | 95.8 | 68.5 |
| Selective ratios (% by weight): | | |
| monomethylamine | 34.7 | 45.6 |
| dimethylamine | 56.3 | 50.8 |
| trimethylamine | 9.0 | 3.6 |

Examples 4 through 6

Using Catalysts 3 through 5, respectively, reactions of ammonia and methanol were conducted in similar way as in Example 1, with the results as shown in Table 1, in which MA, DMA and TMA means monomethylamine, dimethylamine and trimethylamine, respectively.

Example 7

Using Catalyst 6, which has been prepared with a material mixing temperature of 30° C. as shown in Catalyst Preparation 6, the reaction of methanol and ammonia was conducted in similar way as in Example 1, with the results as shown below:

| Methanol conversion ratio: | 89.5% |
|---|---|
| Selective ratios: | |
| monomethylamine | 29% by weight |
| dimethylamine | 57% by weight |
| trimethylamine | 14% by weight |

Example 8

Using Catalyst 7, which has been prepared according to one of prior arts (JP 59-35018A), as shown in Catalyst Preparation 7, the reaction was conducted in similar way as in Example 1, with the results as shown below:

| Methanol conversion ratio: | 83.5% |
|---|---|
| Selective ratios: | |
| monomethylamine | 40% by weight |
| dimethylamine | 38% by weight |
| trimethylamine | 22% by weight |

Comparative Example 1

According to the method mentioned in Catalyst Preparation 1, SAPO-34 was prepared. The SAPO-34 was used, without silica-modification, as catalyst. A reaction was conducted in otherwise similar way as in Example 1, with the results as shown below:

| Methanol conversion ratio: | 83% |
|---|---|
| Selective ratios: | |
| monomethylamine | 30% by weight |
| dimethylamine | 30% by weight |
| trimethylamine | 40% by weight |

Comparative Example 2

Using a silica-alumina catalyst (Nitto Chemical Industry Co., Ltd.: NH-H$_3$N, referred to as "equilibrium-type catalyst"), a reaction was conducted at a temperature of 390° C. under a pressure of 2 MPa with a GHSV of 1,400/h. The results are as follows:

| Methanol conversion ratio: | 99.8% |
|---|---|
| Selective ratios: | |
| momethylamine | 24% by weight |
| dimethylamine | 25% by weight |
| trimethylamine | 51% by weight |

Comparative Examples 3 and 4

Using catalysts which were prepared in similar way as in Catalysts 3 and 4, respectively, but were not silica-modified, reactions of methanol and ammonia were conducted as in Example 1. The results are collectively shown in Table 1.

Example 9

Into a reactor filled with 4.5 g (10 ml volume) of Catalyst 1 was fed a material mixture (monomethylamine containing 10% by weight of methanol) with a space velocity (GHSV : 1/h) of 800, and the reaction was allowed to proceed at a temperature of 320° C. under a pressure of 2 MPa, with the results as below:

| Monomethylamine conversion ratio: | 76% by weight |
|---|---|
| Methanol conversion ratio: | 99.9% by weight |
| Selective ratios: | |
| dimethylamine | 96% by weight |
| trimethylamine | 4% by weight |

Example 10

Into a reactor filled with 2.0 g (4.0 ml volume) of Catalyst 1 was fed monomethylamine with a space velocity (GHSV : 1/h) of 500, and a disproportionation reaction was allowed to proceed at a temperature of 320° C. under a pressure of 2 MPa to form ammonia and dimethylamine. The results are as follows:

| Monomethylamine conversion ratio: | 80.0% |
|---|---|
| Selective ratios: | |
| dimethylamine | 99% by weight |
| trimethylamine | 1% by weight |

Examples 11 through 13

Using Catalysts 2 through 4, respectively, disproportionation reactions of monomethylamine were conducted at a temperature of 320° C. under a pressure of 2 MPa, as in Example 10. The results are collectively listed in Table 1.

Comparative Examples 5 through 8

Using catalysts which were prepared in similar way as in Catalysts 1 through 4, respectively, but were not silica-modified, disproportionation reactions of monomethylamine were conducted as in Example 10. The results are collectively shown in Table 1.

Comparative Example 9

Using silica-modified mordenite, a disproportionation reaction of monomethylamine was conducted as in Example 10. The results are shown in Table 1.

TABLE 1

Results from Examples and Comparative Examples (Production of methylamines)

| Examples | Catalyst | Temp. °C. | GHSV l/h | Conversion (wt. %) | Selectivity (wt. %) | | |
|---|---|---|---|---|---|---|---|
| | | | | | MA | DMA | TMA |
| Ex. 1 | Cat. 1 (silica-mod. SAPO-34) | 320 | 1500 | 99.4 | 35 | 63 | 2 |
| Ex. 2 | Cat. 1 (silica-mod. SAPO-34) | 320 | 3500 | 93.1 | 38 | 61 | 1 |
| Ex. 3 | Cat. 1 (silica-mod. SAPO-34) | 320 | 5000 | 90.4 | 43 | 57 | 0 |
| Ref. 1 | Na-mordenite | 320 | 1420 | 95.8 | 34.7 | 56.3 | 9.0 |
| | Na-mordenite | 320 | 4280 | 68.5 | 45.6 | 50.8 | 3.6 |
| Ex. 4 | Cat. 3 (silica-mod. SAPO-18) | 320 | 1500 | 98.8 | 37 | 61 | 2 |

TABLE 1-continued

Results from Examples and Comparative Examples
(Production of methylamines)

| Examples | Catalyst | Temp. °C. | GHSV l/h | Conversion (wt. %) | Selectivity (wt. %) | | |
|---|---|---|---|---|---|---|---|
| | | | | | MA | DMA | TMA |
| Ex. 5 | Cat. 4 (silica-mod. SAPO-34) | 320 | 1500 | 98.6 | 38 | 60 | 2 |
| Ex. 6 | Cat. 5 (silica-mod. SAPO-34) | 320 | 1000 | 99.6 | 37 | 62 | 1 |
| Ex. 7 | Cat. 6 (silica-mod. SAPO-34) | 320 | 1500 | 89.5 | 29 | 57 | 14 |
| Ex. 8 | Cat. 7 (silica-mod. SAPO-34) | 320 | 1500 | 83.5 | 40 | 38 | 22 |
| Comp. 1 | SAPO-34 | 320 | 1500 | 83.0 | 30 | 30 | 40 |
| Comp. 2 | Equilibrium-type silica-alumina cat. | 390 | 1400 | 99.8 | 24 | 25 | 51 |
| Comp. 3 | SAPO-18 | 320 | 1500 | 82.0 | 28 | 30 | 42 |
| Comp. 4 | CoSAPO-34 | 320 | 1500 | 88.0 | 33 | 30 | 34 |
| Ex. 9 | Cat. 1 (silica-mod. SAPO-34) | 320 | 800 | 76/99.9 | | 96 | 4 |
| Ex. 10 | Cat. 1 (silica-mod. SAPO-34) | 320 | 500 | 80.0 | | 99 | 1 |
| Ex. 11 | Cat. 2 (silica-mod. SAPO-17) | 320 | 500 | 76.8 | | 98 | 2 |
| Ex. 12 | Cat. 3 (silica-mod. SAPO-18) | 320 | 500 | 79.2 | | 98 | 2 |
| Ex. 13 | Cat. 4 (silica-mod. CoSAPO-34) | 320 | 500 | 78.8 | | 97 | 3 |
| Comp. 5 | SAPO-34 | 320 | 500 | 71.0 | | 91 | 9 |
| Comp. 6 | SAPO-17 | 320 | 500 | 70.8 | | 90 | 10 |
| Comp. 7 | SAPO-18 | 320 | 500 | 73.4 | | 90 | 10 |
| Comp. 8 | CoSAPO-34 | 320 | 500 | 67.5 | | 92 | 8 |
| Comp. 9 | silica-mod. mordenite | 320 | 500 | 67.2 | | 69 | 31 |

Example 14

Reference is made to the accompanying drawing.

A reaction was conducted using a primary reactor filled with 20 ml of Catalyst 1 and a secondary reactor also filled with 4ml of Catalyst 1, each at a temperature of 320° C. under a pressure of 2 MPa.

Into the primary reactor were fed methanol and ammonia, together with recycled ammonia from a distillation system containing methylamines, with a space velocity (GHSV : 1/h) of 1580. Monomethylamine separated and recovered from the distillation system was fed to the secondary reactor with a space velocity of 470. The material balance in the process flow is shown in Table 2. In this instance, the amount of dimethylamine formed was 9.1 g per hour.

Comparative Example 10

Reference is also made to the accompanying drawing.

A reaction was conducted using a primary reactor filled with 20 ml of steam-treated Na mordenite (which is prepared according to the description of JP59-227841A) and a secondary reactor filled with 4 ml of a silica-alumina catalyst (manufactured by Nitto Chemical Industry Co., Ltd.: NH-H3N), each at a temperature of 320° C. under a pressure of 2 MPa.

Into the primary reactor were fed methanol and ammonia, together with recycled ammonia from a distillation system containing methylamines, with a space velocity (GHSV: 1/h) of 1,550. Monomethylamine and trimethylamine separated and recovered from the distillation system were fed to the secondary reactor with a space velocity of 800. The material balance in the process flow is shown in Table 2. In this instance, the amount of dimethylamine formed was 6.0 g per hour.

TABLE 2

Material balance (unit: g/h)

| | | Passage No. | | | | | |
|---|---|---|---|---|---|---|---|
| | | 1 | 2 | 3 | 4 | 5 | 6 |
| Ex. 14 | NH$_3$ | 15.5 | 11.3 | | 11.9 | | |
| | MA | 2.3 | 4.3 | 2.6 | 4.8 | | |
| | DMA | | 7.8 | | 9.2 | 0.1 | 9.1 |
| | TMA | | 0.2 | | 0.2 | 0.1 | |
| | MeOH | 13.7 | 0.1 | | 0.1 | | |
| | H$_2$O | | 7.7 | | 7.7 | | |
| | Total | 31.5 | 31.4 | 2.6 | 33.9 | 0.2 | 9.1 |
| Comp. Ex. 10 | NH$_3$ | 15.1 | 11.3 | | 11.3 | | |
| | MA | 2.3 | 4.2 | 0.8 | 5.0 | 0.1 | |
| | DMA | | 6.1 | 0.8 | 6.9 | 0.1 | 6.0 |
| | TMA | | 1.2 | 1.1 | 2.5 | 1.1 | |
| | MeOH | 13.6 | 1.0 | | 1.0 | | |
| | H$_2$O | | 7.0 | | 7.0 | | |
| | Total | 31.0 | 30.8 | 2.7 | 33.7 | 1.3 | 6.0 |

MA: monomethylamine
DMA: dimethylamine
TMA: trimethylamine
MeOH: methanol (Production of lower olefins)

Example 15

Using Catalyst 1 which has been silica-modified, a conversion reaction of methanol to olefins was conducted at a temperature of 420° C. with a methanol feeding rate of WHSV (1/h) 1 under a pressure of 0.1 MPa. The results are shown in Table 3, wherein "Life" means the catalyst life expressed as "hours" until not less than 1% of dimethyl ether was formed.

Example 16

Using Catalyst 7 which has been prepared according to a conventional method and then modified with silica, a reaction was conducted in similar way as in Example 15. The results are shown in Table 3.

Comparative Example 11

Using SAPO-34 made by UOP which has not been silica-modified, a reaction was conducted in similar way as in Example 15. The results are shown in Table 3.

TABLE 3

|  |  | Temp. | Methanol conversion | Selectivity (mol %) | | | | Life |
| --- | --- | --- | --- | --- | --- | --- | --- | --- |
|  |  | ° C. | (mol %) | $C_2'$ | $C_3'$ | $C_4'$ | Total | h |
| Ex. 15 | Cat. 1 | 420 | 100 | 50 | 40 | 4 | 94 | 15 |
| Ex. 16 | Cat. 7 | 420 | 100 | 50 | 32 | 5 | 87 | 9 |
| Comp. 11 | SAPO-34 (made by UOP) | 420 | 100 | 50 | 30 | 7 | 87 | 5 |

$C_2'$: ethylene
$C_3'$: propylene
$C_4'$: butene

What is claimed is:

1. A process for producing methylamines, which comprises contacting methanol and ammonia with a silica-modified crystalline silicoaluminophosphate molecular sieve.

2. A process for producing methylamines, which comprises contacting methanol and monomethylamine with a silica-modified crystalline silicoaluminophosphate molecular sieve.

3. A process for producing methylamines, which comprises contacting a material feed containing one or more methylamines with a silica-modified silicoaluminophosphate molecular sieve, thereby to form methylamines having a higher content of dimethylamine than that in the material feed.

4. The process according to claim 3, wherein the material feed is monomethylamine.

5. A process for producing dimethylamine through a reaction of methanol with ammonia, which comprises Step 1 in which a material mainly composed of methanol and ammonia is subjected to a reaction over a catalyst to form methylamines containing monomethylamine and dimethylamine, and Step 2 in which the monomethylamine obtained in Step 1 is subject to disproportionation reaction over a catalyst to convert it to dimethylamine, wherein at least one of the catalysts in Steps 1 and 2 is a silica-modified crystalline silicoaluminophosphate molecular sieve.

6. A process for producing lower olefins having 2 to 4 carbon atoms, which comprises contacting methanol with a silica-modified crystalline silicoaluminophosphate molecular sieve, thereby to form the lower olefins.

* * * * *